United States Patent [19]

Durrwachter

[11] Patent Number: 5,910,595
[45] Date of Patent: Jun. 8, 1999

[54] PROCESS FOR PREPARING OXIMIDAZOLES

[75] Inventor: J. Robert Durrwachter, Charles City, Iowa

[73] Assignee: Salsbury Chemicals, Inc., Charles City, Iowa

[21] Appl. No.: 09/105,597

[22] Filed: Jun. 26, 1998

[51] Int. Cl.⁶ ..................... C07D 233/32; C07D 235/02
[52] U.S. Cl. .................... 548/300.7; 548/316.4; 548/325.5
[58] Field of Search .............. 548/316.4, 325.5, 548/300.7

[56] References Cited

U.S. PATENT DOCUMENTS

| | | | |
|---|---|---|---|
| 4,709,036 | 11/1987 | Los et al. | 546/167 |
| 5,424,450 | 6/1995 | Boswell et al. | 548/253 |
| 5,698,704 | 12/1997 | Jackson | 548/300.7 |

FOREIGN PATENT DOCUMENTS

| | | |
|---|---|---|
| 205879 | 12/1986 | European Pat. Off. . |
| 789019 | 8/1997 | European Pat. Off. . |

OTHER PUBLICATIONS

Oniciu et al, Rev. Roumaine de Chem. "Synthesis of Substituted 2–Oxazolin–4–ones and 1–Imidazolin–5–ones", 37(3) 407–409 (1992).

Poupaert et al, Synthesis, "N–Acyl– –amininitriles In The Pinner Reaction", 622–624 (1972).

Li et al, Tetrahedron, "Asymetric Synthesis And Absolute Stereochemistry Of 4,4–Bis(trifluoromethyl)–imidazoline etc." 53(15), 5359–5372 (1997).

Li et al, J. Org. Chem., An Unusual Trifuoromethyl Elimination Reaction From The 4,4–Bis(trifluoromethyl)–5–hydroxyimidazoline Ring System, 62, 2550–2554 (1997).

*Primary Examiner*—Floyd D. Higel
*Attorney, Agent, or Firm*—Richard J. Hammond

[57] ABSTRACT

A process is disclosed for the preparation of an imidazolone and the pharmaceutically acceptable salts thereof having the formula

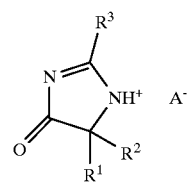

1 wherein R1 and R2 are the same or different and are C1 to C6 alkyl, C2 to C6 alkenyl, C1 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo;

or R1 and R2 taken together with the carbon atom in the imidazolone ring form a carbocyclic or heterocyclic ring having from three to seven members and is saturated or is at least mono unsaturated;

R3 is C1 to C6 alkyl, C2 to C6 alkenyl, C3 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo; and A- is an anion of an organic or inorganic acid. The process comprises treating an α-acylaminonitrile of the formula

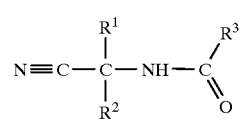

2 wherein R1, R2 and R3 are as defined above with an organic or inorganic acid having the formula HA where A is as defined above in a nonaqueous solvent and in the presence of an alcohol of the formula R—OH where R is C5 to C12 alkyl, C5 to C12 alkenyl, C3 to C12 cycloalkyl, poly alkylene ether, poly alkylene thio ether or aryl either unsubstituted or substituted with at least one C1 to C6 alkyl, C1 to C6 alkoxy or halo.

15 Claims, No Drawings

PROCESS FOR PREPARING OXIMIDAZOLES

FIELD OF INVENTION

This invention relates to a process for preparing oximidazolones having substituents at positions 2 and 5 of the ring. More particularly, this inventions relates to a process for preparing 1,3 -(2,5-disubstituted) oximidazol-4-one compounds and the pharmaceutically acceptable salts thereof

BACKAROUND OF THE INVENTION

U.S. Pat. No. 4,709,036 discloses herbicidal 2-(4,4-disubstituted 5-oxo-2-imidazolin-2-yl) benzoic acids of the formula

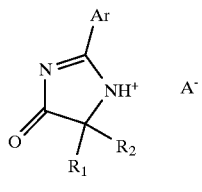

1a where Ar is a substituted or unsubstituted aromatic or heteroaromatic group, R1 and R2 are alkyl or taken together are cycloalkyl. These imidazolones are prepared by cyclization of α-amidonitriles of the formula

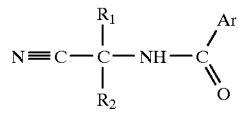

where Ar, R1 and R2 are defined above.

Compounds of Formula 1a have proven successful as herbicides, demonstrated. Also see for example, U.S. Pat. No. 5,424,450 In the process to produce the pharmaceutically-active imidazolones, the cyclization of the amidonitrile is carried out in a chlorinated hydrocarbon solvent saturated with an excess of a hydrogen halide at a temperature of from 0° to 130° C. under anhydrous conditions.

Verschave et al, *Tetrahedron*, 40, 2395–04 (1984) discloses that compounds of Formula 1, above, where Ar is phenyl, R1 is methyl and R2 is 3-methoxyphenyl can be formed by the cyclization of the nitrile of Formula 2 (where Ar, R1 and R2 are as previously defined in the presence of hydrogen chloride and o-dichlorobenzene (with heat). See also, Oniciu et al, *Rev Rhom Chim*,37 (3), 407–09 (1992) and Roes ter et al, *Bull Soc Chim France*, 1967(12), 4624–31 for nitrile cyclizations in similar solvents.

Shiria et al, *J Synthetic Org Chem Japan*, 31 (1), 88–93 (1973) discloses a process to prepare the compounds of Formula 1 where Ar may be aryl, alkyl and aralkyl and R1 and R2 include an alkyl group. The process involves the cyclization of nitrites of Formula 2, where the substituents are as defined above, such cyclization being conducted in a chloroform solution with methanol or ethanol and hydrogen chloride. Also see U.S. Pat. No. 5,424,450, referred to above and WO 91/14,679 for similar reactions.

EP 0 789 019 Al discloses the cyclization of amidonitriles of Formula 2 where Ar includes alkyl and R1 and R2 taken together with the carbon atom on which they are substituted form a carbocyclic ring. The cyclized compounds are 4-oxoimidazolones and their salts. Significantly, the cyclization occurs by the action of a strong acid, such as hydrogen chloride in a water-free solution of a lower alcohol, which may also act as a solvent for this reaction. The "lower alcohol" is defined in the specification as a C1 to C4 alcohol, further defined as methanol, ethanol, propanol, butanol and isopropyl alcohol.

While EP 0 789 019 Al is successful in producing the required cyclic compounds, yields of such products are not as great as desired. There is therefore a need for an alternate process offering greater product production.

SUMMARY

A process for the preparation of an imidazolone and the pharmaceutically acceptable salts thereof having the formula

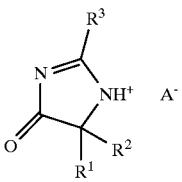

1 wherein R1 and R2 are the same or different and are C1 to C6 alkyl, C2 to C6 alkenyl, C1 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo;

or R1 and R2 taken together with the carbon atom in the imidazolone ring form a carbocyclic or heterocyclic ring having from three to seven members and is saturated or is at least mono unsaturated;

R3 is C1 to C6 alkyl, C2 to C6 alkenyl, C3 to C6 cycloalkyl, aryl either unsubstituted or substituted with at least one substituent selected from the group consisting of C1 to C6 alkyl, C1 to C6alkoxy and halo or heteroaryl either unsubstituted or substituted with Cl to C6 alkyl or halo; and A- is an anion of an organic or inorganic acid is disclosed. The process comprises treating an α-acylaminonitrile of the formula

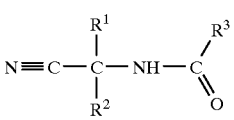

2 wherein R1, R2 and R3 are as defined above with an organic or inorganic acid having the formula HA where A is as defined above in a nonaqueous solvent and in the presence of an alcohol of the formula R—OH where R is C5 to C12 alkyl, C5 to C12 alkenyl, C3 to C12 cycloalkyl, poly alkylene ether, poly alkylene thio ether or aryl either unsubstituted or substituted with at least one C1 to C6 alkyl, C1 to C6 alkoxy or halo.

DESCRIPTION OF THE PREFERRED EMBODIMENTS

In the following specification, the following definitions apply:

The term "C1 to C6 alkyl" is intended to mean the monovalent linear or branched hydrocarbon groups having from 1 to 6 carbon atoms, such including the groups methyl, ethyl, n-propyl, isopropyl, n-butyl, sec-butyl, t-butyl, n-pentyl isopentyl, neopentyl, n-hexyl, 1,2-dimethylbutyl, 2,2-dimethylbutyl, 2-ethylbutyl and the like.

The term "C5 to C12 alkyl" is intended to mean the monovalent linear or branched hydrocarbon groups having from 5 to 12 carbon atoms, such including the groups pentyl, isopentyl, neopentyl, n-hexyl, 1,2-dimethylbutyl, 2,2-dimethylbutyl, 2-ethylbutyl, n-heptyl, 2,2,3trimethylbutyl, 2,3,3-trimethylbutyl, 2-methyl-3-ethylbutyl, 2-ethyl-3-methylbutyl, n-octyl, 2,2,3,3-tetramethylbutyl, 2,2-dimethyl-3-ethylbutyl, 2-ethyl-3,3-dimethylbutyl, n-nonyl, 2,2,3,3tetramethylpentyl, n-decyl, 2,2,3,3-tetramethylhexyl, n-undecyl and the like.

The term "C2 to C6 alkenyl" is intended to mean the monovalent linear or branched hydrocarbon groups having from 2 to 6 carbon atoms, such including the groups vinyl, 1-propenyl, allyl, isopropenyl, 1-butenyl, 2-butenyl, 1-pentenyl, 2-pentenyl, 2-methyl-2-pentenyl, 1-hexenyl, 2-methyl-2-pentenyl and the like.

The term "C5 to C12 alkenyl" is intended to mean the monovalent linear or branched hydrocarbon groups having from 5 to 12 carbon atoms, such including the groups 1-pentenyl, 2-pentenyl, 2-methyl-2-pentenyl, 1--hexenyl, 2-methyl-2-pentenyl, 1-heptenyl, 2-methyl-2-hexenyl, 1-octenyl, 2-methyl-2-heptenyl, 1-decenyl, 2-methyl-2-nonenyl and the like, The term "C3 to C7 cycloalkyl" is intended to mean the monovalent unsubstituted or C1 to C6 alkyl-substituted carbocyclic hydrocarbons having from 3 to 7 total ring carbon atoms, such including the groups cyclopropyl, cyclobutyl, cyclopentyl, 2-methylcyclopentyl, cyclohexyl and the like.

The term "C5 to C12 cycloalkyl" is intended to mean the monovalent unsubstituted or C5 to C12 alkyl-substituted carbocyclic hydrocarbons having from 5 to 12 total carbon atoms, such including cyclopentyl, 2-methylcyclopentyl, cyclohexyl, 2-methylcyclohexyl, cycloheptyl, 2--methylcycloheptyl, cyclooctyl, 2-methylcyclooctyl and the like.

The term "aryl either unsubstituted or substituted with at least one substituent selected from the group consisting of C1 to C6 alkyl, C1 to C6 alkoxy and halo" is intended to mean the groups phenyl or naphthyl either unsubstituted or substituted with one or more of the groups illustrated by the C1 to C6 alkyl as defined above, methoxy, propoxy, fluoro, chloro and the like.

The term "heteroaryl either unsubstituted or substituted with C1 to C6 alkyl or halo" is intended to mean the groups furanyl, thiophenyl, pyrrolyl, pyranyl, pyrindinyl, and the like either unsubstituted or having one or more substituents that are C1 to C6 alkyl as defined above or halo selected from the group consisting of fluoro, chloro, bromo and iodo.

The term "poly alkylene ether" is intended to mean componds having the general formula H[O(CH$_2$)$_n$]$_y$— where n is an integer from 2 to 12 and y is an integer from 1 to 1000.

The term "poly alkylene thioether" is intended to mean the above-defined poly alkylene ether compounds having a least one of the oxygen atoms on the chain replaced by a sulfur atom.

In the following specification, the process in carried out in accordance with the present invention utilizes an acid, sometimes referred to as a "strong acid", having the formula HA. These acids include either organic or inorganic acids. The former are acids such illustrated by acetic acid substituted with at least one halo group, citric acid, formic acid and sulfonic acid, either unsubstituted or substituted with C1 to C6 alkyl or unsubstituted or substituted with aryl as defined above and the like. The latter acids are illustrated by the hydrogen halides (hydrogen fluoride, hydrogen chloride, etc.), sulfuric acid, phosphoric acid and the like.

The present invention is a process to prepare substituted imidazolones and the pharmaceutically acceptable salts thereof having the formula

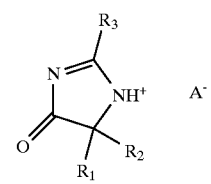

wherein R1 and R2 are the same or different and are C1 to C6 alkyl, C2 to C6 alkenyl, C3 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo;

or R1 and R2 taken together with the carbon atom in the imidazolone ring form a carbocyclic or heterocyclic ring having from three to seven members and is saturated or is at least mono unsaturated;

R3 is C1 to C6 alkyl, C2 to C6 alkenyl, C3 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo;

and A is an anion of an organic or inorganic acid.

In the imidazolone (free base) and pharmaceutically acceptable salts thereof, it is preferred that R1 and R2 are the same or different and are C1 to C3 alkyl, most preferably methyl or ethyl or that R1 and R2 are taken together with the carbon atom in the ring to form a spirocyclopentyl or spirocyclohexyl group, most preferably a spirocyclopentyl group.

Preferably R3 is C1 to C6 alkyl, most preferably n-propyl or n-butyl A particularly preferred imidazolone salt formed in the process of the present invention has the formula

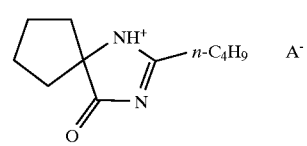

where A is as defined above.

The process to prepare the imidazolone compounds and the pharmaceutically acceptable salts thereof involves the cyclization of an α-amidonitrile of the formula

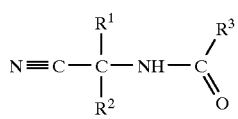

where R1, R2 and R3 are as defined above in the the imidazolone compounds. These compounds are well known in the prior art and their preparation is disclosed in numerous patents and publications. For example, see U.S. Pat. No. 5,424,450.

In the α-amidonitrile starting materials in accordance with the present invention, it is preferred that R1 and R2 are the same or different and are C1 to C3 alkyl, most preferably methyl or ethyl.

Preferably R3 is C1 to C6 alkyl, most preferably n-propyl or n-butyl.

In the process of the present invention, a substantially anhydrous solution of the α-amidonitrile (Formula 2) is heated in the presence of an alcohol of the formula ROH where R is C5 to C12 alkyl, C5 to C12 alkenyl, C5 to C12 cycloalkyl, poly alklene ether, poly alkylene thio ether or aryl either unsubstituted or substituted with at least one C1 to C6 alkyl, C1 to C6 alkoxy or halo and an organic or inorganic acid having the formula HA, as defined above.

The term "substantially anhydrous" is intended to mean that the components of the solution, e.g., the amidonitrile, the alcohol ROH, the acid HA and the solvent (if not the same as the alcohol ROH) either individually or when admixed into the solution do not contain water at a concentration that would interrer with the cyclization reaction and the formation of the compounds of Formula 1. Concentrations of water in the reaction (cyclization) solution of less than 1 % are preferred and less than 0.5% are most preferred.

In the alcohol having the formula ROH as defined above, it is preferred that R is pentyl, isopentyl, neopentyl, n-hexyl, 1,2-dimethylbutyl, 2,2-dimethylbutyl, 2-ethylbutyl, n-heptyl, 2,2,3-trimethylbutyl, 2,3,3-trimethylbutyl, 2-methyl-3-ethylbutyl, 2-ethyl-3-methylbutyl, n-octyl, 2,2, 3,3-tetramethylbutyl, 2,2-dimethyl-3-ethylbutyl, 2-ethyl-3, 3-dimethylbutyl, n-nonyl, 2,2,3,3-tetramethylpentyl, n-decyl, 2,2,3,3-tetramethylhexyl, n-undecyl n-dodecyl, cyclopentyl, 2-methylcyclopentyl, cyclohexyl, 2-methylcyclohexyl, cycloheptyl, 2-methylcycloheptyl, cyclooctyl, 2-methylcyclooctyl, poly(ethylene ether) oxy of molecular weight between 200 and 1000, phenoxy and α-naphthoxy. Most preferably R is n-pentyl, n-hexyl, n-heptyl, n-octyl, 2-methylbutyl or cyclohexyl.

The solvent used to form the solution in which the cyclization of the amidonitrile occurs may be the alcohol ROH, as noted above, or it may be a different (substantially anhydrous) organic material that is a liquid at the recation temperature and does not interrer with the cyclization reaction. As such, the organic solvent may be an aromatic solvent, e.g., benzene, toluene, xylene, etc., a hydro carbon solvent, opt ion ally halogenated, e.g., hexane, octane, monochloroethane, dichloroethane, etc.

The temperature of the amidonitrile cyclization reaction is from about 0° to about 120° C., preferably from about 200 to about 100° C., most preferably from about 25° to about 50° C.

The following Examples are for the purposes of illustration only and should not be regarded as a limitation on the scope of the invention described and claimed herein.

EXAMPLES

Example 1

A 500 mL round bottom flask is fitted with thermowell, nitrogen atmosphere, magnetic stirring and addition funnel. Into the flask is charged 11.9% HCl in 1-octanol(235 g solution,28 g HCl). 1-Valeramidocyclopentane carbonitrile solution in toluene (80.2 g @ 84.1 % carbonitrile, 67.4g, 0.347 mole) is charged to the addition funnel. The carbonitrile solution is added to the acidic alcohol over about 15 minutes, maintaining the temperatures 25° C. After the addition is complete, the reaction is warmed to35–45° C. for 16 hours. The slurry is cooled to 6° C.,filtered and washed with 1-octanol(2×50 mL)to yield 82.35 g wet cake, Yield! 82,35 g @ 16.27% LOD=68.95 g dry (0.299 mole), 86% yield@

Example 2

A 500 mL round bottom flask is fitted with tbermowell, nitrogen atmosphere, magnetic stirring and addition funnel. Into the flask is charged 12.2% HCl in 1-hexanol (229 g solution, 28 g HCl). 1-Valeramidocyclopentane carbonitrile solution in toluene (60.15 @ 84.1 % carbonitrile, 67.4 g, 0.347 mole) is charged to the addition funnel. The carbonitrile solution is added to the acidic alcohol over about 25 minutes, maintaining the temperature around 35° C. After the addition is complete, the reaction is maintained at 35° C. for 10 hours, then cooled to room temperature for 64 hours. The slurry is cooled in an icebath, filtered and washed with 1-hexanol(2×50 mL) to yield 67.2 g. Yield: 67.2 g(0.291 mole), 94% yield.

Example 3

A 1000 mL round bottom flask is fitted with thermowell, nitrogen atmosphere, magnetic stirring and addition funnel. Into the flask is charged 13.2% HCl in 1-pentanol (212 g solution, 27.9 g HCl). 1-Valeramidocyclopentane carbonitrile solution in toluene (81.2 g @ 94.1% carbonitrile, 69.3g, 0 351 mole) is charged to the addition funnel. The carbonitrile solution is added to the acidic alcohol over about 10 minutes, maintaining the temperature 35–40° C. After the addition is complete, the reaction is maintained at 35° C. for 10 hours, then cooled to room temperature for about 8 hours. The slurry is cooled in an ice bath to 5° C., filtered and washed with 1-pentanol (2×50 mL) to yield after drying 65.8 g material (0.285 mole), 91% yield.

Example 4

A 1000 mL round bottom flask is fitted with a thermowell, nitrogen atmosphere, mechanical stirring and addition funnel. Into the flask is charged 10.9% HCl in isoamyl alcohol (257.4 g solution, 28 g HCl). 1-Valeramidocyclopentane carbonitrile solution in toluene (80.37 g @ 84.1% carbonitrile, 67-6g, 0.348 mole) is charged to the addition funnel. The carbonitrile solution is added to the acidic alcohol over about 30 minutes, maintaining the temperature around 35° C. During the addition, an exotherm elevated the reaction temperature to 49° C. After the addition is complete, the reaction is maintained at 35° C. for 1 hour hours, then cooled to room temperature for about 64 hours. The slurry is cooled in an ice bath to 50° C., filtered and washed with isoamyl alcohol (2×50 mL) to yield 67.99 g wet cake (LOD 1.94%; yield 66.67 g, 0.289 mole, 83% yield.

Example 5

A 1000 mL round bottom flask is fitted with thermowell, nitrogen atmosphere, mechanical stirring and addition funnel. Into the flask is charged 11.6% HCl in cyclohexanol (249.4 g solution, 28.9 g HCl). 1-Valeramidocyclopentane carbonitrile solution in toluene (92.96 g @ 94.1% carbonitrile, 69.7 g, 0.359 mole) is charged to the addition funnel. The carbonitrile solution is added to the acidic alcohol over about 30 minutes, maintaining the temperature around 35° C. After the addition is complete, the reaction is maintained at 33° C. for 16 hours, then cooled to room temperature overnight. The slurry is cooled in an ice bath to 5° C., filtered and washed with cyclohexanol (1×50 ml, 1×100 ml) to yield 86.75 g wet cake (LOD 23.6%, yield: 66 28 g, 0.287 mole, 80% yield.

Example 6 (Comparative)

A 1000 mL round bottom flask is fitted with thermowell, nitrogen atmosphere, mechanical stirring and addition funnel. Into the flask is charged 12.32% HCl in 1-propanol (227 g solution, 28 g HCl), 1-Valeramidocyclopentane carbonitrile solution in toluene (109.96 g @ 85.3% carbonitrile, 93.8 g, 0.483 mole) is charged to the addition funnel; 1-propanol (19.33 g) is used to make the transfer quantitative. The carbonitrile solution is added to the acidic alcohol over about 10 minutes, maintaining the temperature 20–24° C. After the addition is complete, the reaction is warmed to 30–35° C. for 6 hours, then cooled to room temperature for 15 hours. The slurry is cooled in an ice bath to 6° C., filtered and washed with 1-propanol (2×50 mL) and sucked dry on the filter to yield 80.33 g of crude product (yield—80.33 g, 0.348 mole, 72% yield).

Example 7 (Comparative)

A 1000 mL round bottom flask is fitted with thermowell, nitrogen atmosphere, mechanical stirring and addition funnel. Into the flask is charged 14.35% HCl in 1-propanol (195.1 g solution, 28 g HCl). 1-Valeramidocyclopentane carbonitrile solution in toluene (132.2 g @ 72% carbonitrile, 95.2 g, 0.490 mole) is charged to the addition funnel. 1-propanol (30 mL) is used to make the transfer quantitative. The carbonitrile solution is added to the acidic alcohol over about 50 minutes, maintaining the temperature 20–25° C. After the addition is complete, the reaction is warmed to 30–41° C. for 6 hours, then cooled to room temperature for 15 hours. The slurry is cooled in an ice bath to 4° C., filtered and washed with 1-propanol (2×50 mL) to yield 88.6 g of crude product (LOD 4%; yield: 85.1 g, 0.369 mole, 75% yield).

I claim:

1. A process for the preparation of an imidazolone or the pharmaceutically acceptable salts thereof having the formula

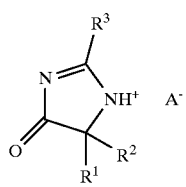

wherein R, and R2 are the same or different and are C1 to C6 alkyl, C2 to C6 alkenyl, C1 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo;

or R1 and R2 taken together with the carbon atom in the imidazolone ring form a carbocyclic or heterocyclic ring having from three to seven members and is saturated or is at least mono unsaturated;

R3 is C1 to C6 alkyl, C2 to C6 alkenyl, C3 to C6 cycloalkyl, aryl either unsubstituted or substituted with at least one substituent selected from the group consisting of C1 to C6 alkyl, C1 to C6 alkoxy and halo or heteroaryl either unsubstituted or substituted with C1 to C6 alkyl or halo; and A is an anion of an organic or inorganic acid, said process comprising reacting an acylaminonitrile of the formula

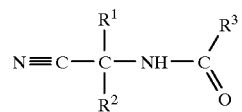

wherein R1, R2 and R3 are as defined above with an organic or inorganic acid having the formula HA where A is as defined above in a nonaqueous solvent and in the presence of an alcohol of the formula R—OH where R is C5 to C12 alkyl, C5 to C12 alkenyl, C5 to C12 cycloalkyl, poly alkylene ether, polyalkylene thioether or aryl either unsubstituted or substituted with at least one C1 to C6 alkyl, C1 to C6 alkoxy or halo.

2. The process according to claim 1 wherein said acid is an inorganic acid selected from the group consisting of hydrogen halide, sulfuric acid and phosphoric acid.

3. The process according to claim 1 wherein said acid is an organic acid selected from the group consisting of acetic acid substituted with at least one halogen, citric acid, formic acid and sulfonic acid either unsubstituted or substituted with C1 to C6 alkyl or aryl.

4. The process according to claim 1 wherein said alcohol is the nonaqueous solvent.

5. The process according to claim 4 wherein R is C5 to C12 alkyl.

6. The process according to claim 5 wherein ROH is 1-octanol, 1-heptanol,1-hexanol or 1-pentanol.

7. The process according to claim 1 wherein R1 and R2 are taken together with the carbon atom in the imidazolone ring to form a carbocyclic ring having from three to seven members that is saturated or is at least mono unsaturated.

8. The process according to claim 7 wherein R1 and R2 are taken together with the carbon atom in the imidazolone ring to form a cyclopentane ring or a cyclohexane ring.

9. The process according to claim 1 wherein R3 is C3 to C6 alkyl.

10. The process according to claim 9 wherein R3 is n-butyl.

11. A process for the preparation of an imidazolone or the pharmaceutically acceptable salts thereof having the formula

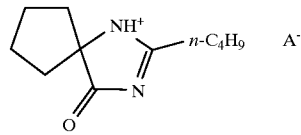

wherein A is the anionic part of an organic or inorganic acid, said process comprising reacting an α-acylaminonitrile of the formula

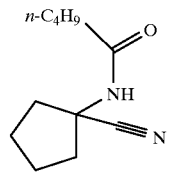

with an organic or inorganic acid having the formula HA where A is as defined above in a nonaqueous solvent and in the presence of an alcohol having the formula R—OH where R is C5 to C 12 alkyl.

12. The process according to claim 11 wherein said said alcohol is utilized as the nonaqueous solvent.

13. The process according to claim 12 wherein said alcohol is 1-pentanol.

14. A process for preparing an imidazolone or the pharmaceutically acceptable salts thereof having the formula

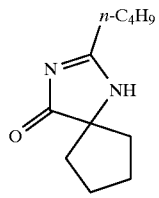

said process comprising, reacting an α-acylaminonitrile of the formula

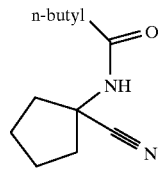

with an acid that is an organic acid selected from the group consisting of acetic acid substituted with at least one halo group, citric acid, formic acid, sulfonic acid either unsubstituted or substituted with $C_1$ to $C_6$ alkyl and substituted or unsubstituted aryl or an inorganic acid selected from the group consisting of hydrogen halide, sulfuric acid and phosphoric acid in a nonaqueous solvent selected from the group consisting of an alcohol of the formula ROH, wherein R is $C_5$ to $C_{12}$ alkyl, $C_5$ to $C_{12}$ alkenyl, $C_5$ to $C_{12}$ cycloalkyl, polyalkylene ether, polyalkylene thioether and substituted or unsubstituted aryl, said substituents being at least one $C_1$ to $C_6$ alkyl, $C_1$ to $C_6$ alkoxy, or halo in the presence of said alcohol, said reacting being carried out at a temperature of from about 25° to about 50° C.

15. The process according to claim 14 wherein said acid is hydrochloric acid, said non aqueous solvent is the alcohol that said reaction is carried out in the presence of and is 1-pentanol and the temperature of said reacting is 33° to 45° C.

* * * * *